United States Patent [19]
Wilk et al.

[11] Patent Number: 5,397,354
[45] Date of Patent: Mar. 14, 1995

[54] METHOD AND DEVICE FOR REMOVING A TOXIC SUBSTANCE FROM BLOOD

[76] Inventors: Peter J. Wilk, 185 West End Ave., New York, N.Y. 10023; Steven J. Gruber, 19 Dogwood Rd., Albertson, N.Y. 11507

[21] Appl. No.: 168,050

[22] Filed: Dec. 15, 1993

Related U.S. Application Data

[63] Continuation-in-part of Ser. No. 932,368, Aug. 19, 1992, Pat. No. 5,322,503.

[51] Int. Cl.⁶ .............................................. A61F 2/04
[52] U.S. Cl. ...................................... 623/11; 623/66; 604/28
[58] Field of Search ................... 604/4, 5, 27, 29; 623/11, 12, 66

[56] References Cited

U.S. PATENT DOCUMENTS

| | | | |
|---|---|---|---|
| 3,505,686 | 4/1970 | Bodell | 623/66 |
| 4,235,231 | 11/1980 | Schindler | 604/4 |
| 4,354,933 | 10/1982 | Lester | 604/5 |
| 4,416,657 | 11/1983 | Berglund | 604/29 |
| 4,437,856 | 3/1984 | Valli | 604/29 |
| 4,588,407 | 5/1986 | Isono et al. | 623/11 |
| 4,769,037 | 9/1988 | Midcalf | 623/12 |
| 5,037,385 | 8/1991 | O'Byrne | 604/29 |
| 5,092,886 | 3/1992 | Dobos-Hardy | 623/12 |
| 5,106,365 | 4/1992 | Hernandez | 604/27 |
| 5,284,470 | 2/1994 | Beltz | 623/66 |

Primary Examiner—Ralph A. Lewis
Attorney, Agent, or Firm—R. Neil Sudol; Henry D. Coleman

[57] ABSTRACT

A method for removing a toxic substance from a patient utilizes a filtering device defining a first fluid flow path and a second fluid flow path. The filtering device also includes a semipermeable membrane separating the first fluid flow path and the second fluid flow path from one another, the membrane being selectively permeable to the toxic substance. The filtering device additionally includes a reservoir and a pump, the reservoir being located along the second fluid flow path between the membrane and the second inlet port. The filtering device is inserted into the patient so that it is totally surrounded by the patient, the filtering device is connected to a blood vessel of the patient so that blood from the artery is shunted along the first fluid flow path. An outlet end of the second fluid flow path is connected to the urinary bladder of the patient. The inlet end of the second fluid flow path is disposed at the skin surface of the patient to enable a periodic refilling of the reservoir with a working fluid. Upon installation of the filtering device in the patient, the pump is operated to transfer working fluid along the second fluid flow path from the reservoir to the urinary bladder of the patient while blood flows along the first fluid flow path, thereby enabling transfer of the toxic substance from the patient's blood through the membrane to the working fluid in the second fluid flow path.

14 Claims, 2 Drawing Sheets

METHOD AND DEVICE FOR REMOVING A TOXIC SUBSTANCE FROM BLOOD

CROSS-REFERENCE TO A RELATED APPLICATION

This application is a continuation-in-part of application Ser. No. 07/932,368, filed Aug. 19, 1992, now U.S. Pat. No. 5,322,503.

BACKGROUND OF THE INVENTION

This invention relates to a method and to an associated device for automatically removing a toxic substance from a person's blood.

There are presently some 175,000 people in the United States on renal dialysis, up from 100,000 three years ago. Approximately ten percent of the national health budget is allotted to pay for dialysis. Dialysis removes toxins from a patient's blood supply and also removes excess salt and water.

There are currently two principal types of dialysis. Hemodialysis guides blood from a shunt in a person's arm to a filtering machine. The filtered blood is then returned to the patient. In peritoneal dialysis, a fluid is injected into the peritoneal cavity through a thin tube. The peritoneal lining serves as a filter, allowing metabolic toxins from the blood to enter the working fluid in the peritoneal cavity. The fluid is replaced four to six times a day, seven days a week.

Conventional dialysis techniques involve some substantial disadvantages. In hemodialysis, the patient is connected to the filtration machine three continuous hours three times a week. Appointments must be made substantially in advance. The patient's travel opportunities are accordingly severely curtailed. Moreover, hemodialysis is stressing to the heart. Strokes and even death can occur during the procedure. Heparin, a blood thinner or anticlotting agent, must be injected into the patient's blood stream with the possible side effect of bleeding in the brain.

In peritoneal dialysis, peritonitis (infection) is a significant problem. An infection occurs once every sixteen patient months. Also the frequent exchange of the filtrate fluid is cumbersome.

One alternative to conventional dialysis is a kidney transplant. The big problem with such a solution is the necessity of taking medication to prevent rejection of the transplant. Side effects of the drugs include infection, stomach ulcers, weakening of kidney function, and cancer.

It is to be noted that there are many toxins produced by the body which must be metabolized or otherwise eliminated. Many people are born without the ability to eliminate one or more of these toxins. For example, Gaucher's disease entails storage of excessive amounts of glucocerebroside and results eventually in an enlarged liver and spleen and neurological lesions. Nieman-Pick disease involves the excessive storage of phospholipids especially sphingomyelin. Nieman-Pick disease also results in an enlarged liver and spleen, as well as mental retardation and convulsions. In Tay-Sachs disease, there is a build-up of gangliosidoses, which results in blindness and dementia. Death in childhood may be a consequence of any of these three diseases. Other congenital diseases are known which entail the concentration of toxic substances in the body.

U.S. Pat. No. 5,322,503 (application Ser. No. 07/932,368) is directed to a medical method for providing nutrition to a patient. The method of that patent utilizes a container which is implanted intra-abdominally and serves as a reservoir for a total nutrition fluid. The container has an inlet port component disposable in the person's abdominal wall for enabling a periodic refilling of the container. A pump is mounted to the container for periodically pumping an aliquot of a liquid nutrient from the container to a selected vein of the portal vein system.

It has been discovered in conjunction with the present invention that the intra-abdominal reservoir of U.S. Pat. No. 5,318,519 may be useful for treating other kinds of debilitating conditions.

OBJECTS OF THE INVENTION

An object of the present invention is to provide an alternative to hemodialysis and peritoneal dialysis for cleaning the blood of metabolic toxins.

Another, more particular, object of the present invention is to provide such a method which provides greater freedom to patients than conventional dialysis techniques.

A further particular object of the present invention is to provide such a method which is less expensive than conventional dialysis.

Another object of the present invention is to provide a method for eliminating toxins which are not otherwise eliminated naturally.

Yet another object of the present invention is to provide a device for implementing the method of the invention.

These and other objects of the present invention will be apparent from the drawings and detailed descriptions herein.

SUMMARY OF THE INVENTION

A method for removing a toxic substance from a patient utilizes, in accordance with the present invention, a filtering device including a first fluid flow path having a first inlet port and a first outlet port and further including a second fluid flow path having a second inlet port and a second outlet port. The filtering device also includes a semipermeable membrane separating the first fluid flow path and the second fluid flow path from one another, the membrane being selectively permeable to the toxic substance. The filtering device additionally includes a reservoir and a pump, the reservoir being located along the second fluid flow path between the membrane and the second inlet port. The method includes the steps of inserting the filtering device into the patient so that the filtering device is totally surrounded by the patient, connecting the first inlet port and the first outlet port to a blood vessel of the patient at spaced points along the blood vessel, and attaching the second outlet to the urinary bladder of the patient. The second inlet port is disposed at the skin surface of the patient to enable a periodic refilling of the reservoir with a working fluid. Upon installation of the filtering device in the patient, the pump is operated to transfer working fluid along the second fluid flow path from the reservoir to the urinary bladder of the patient while blood flows along the first fluid flow path, thereby enabling transfer of the toxic substance from the patient's blood through the membrane to the working fluid in the second fluid flow path.

According to another feature of the present invention, the method further comprises the step of filling the reservoir with working fluid via the second inlet port. This filling takes place periodically and may be done at home by the patient or user or on an outpatient basis at a hospital.

According to a further feature of the present invention, the semipermeable membrane is replaced after use of the filtering device. The semipermeable membrane may be removed from the filtering device through an additional port provided at the patient's skin surface, a new semipermeable membrane being subsequently inserted through the additional port.

A medical treatment assembly for removing a toxic substance from a patient comprises, in accordance with the present invention, a filtering device including a housing defining a first fluid flow path and a second fluid flow path. The housing is disposed completely within the patient, while the filtering device is connected to a blood vessel of the patient so that blood from the blood vessel flows along the first fluid flow path. A semipermeable membrane is provided in the housing to separate the first fluid flow path and the second fluid flow path from one another, the membrane being selectively permeable to the toxic substance. A reservoir is disposed along second fluid flow path upstream of the membrane, the reservoir also being disposed completely within the patient. A pump is operatively connected to the filtering device to pump a working fluid along the second fluid flow path from the reservoir and past the semipermeable membrane, thereby enabling transfer of the toxic substance from the patient's blood through the membrane to the working fluid in the second fluid flow path. The housing is connected to the patient's urinary bladder so that working fluid with the filtered toxic substance flows from the housing to the patient's urinary bladder.

A method for removing a toxic substance from blood comprises, in accordance with the present invention, the steps of guiding blood from a person's vascular system to a filtering device, filtering the toxic substance from the blood flowing through the filtering device to thereby clean the blood of the toxic substance, returning the cleaned blood to the person's vascular system upon filtering of the toxic substance from the blood flowing through the filtering device, and feeding the filtered toxic substance to the person's urinary bladder.

According to another feature of the present invention, the steps of guiding, filtering, returning and feeding all take place within the person's abdominal cavity.

According to another feature of the present invention, the step of filtering includes the steps of directing a working fluid through the filtering device and selectively passing the toxic substance through a semipermeable membrane to the working fluid from the blood flowing through the filtering device. The working fluid may be pumped from a reservoir inside the person's abdominal cavity.

A method in accordance with the present invention provides an alternative to hemodialysis and peritoneal dialysis for cleaning the blood of metabolic toxins. The present method is less expensive and more convenient than conventional dialysis.

A method and device in accordance with the present invention also serves for eliminating other toxins which are not otherwise eliminated naturally owing, for example, to a genetic lack of an enzyme or other metabolic requirement.

DETAILED DESCRIPTION

Figure 1:
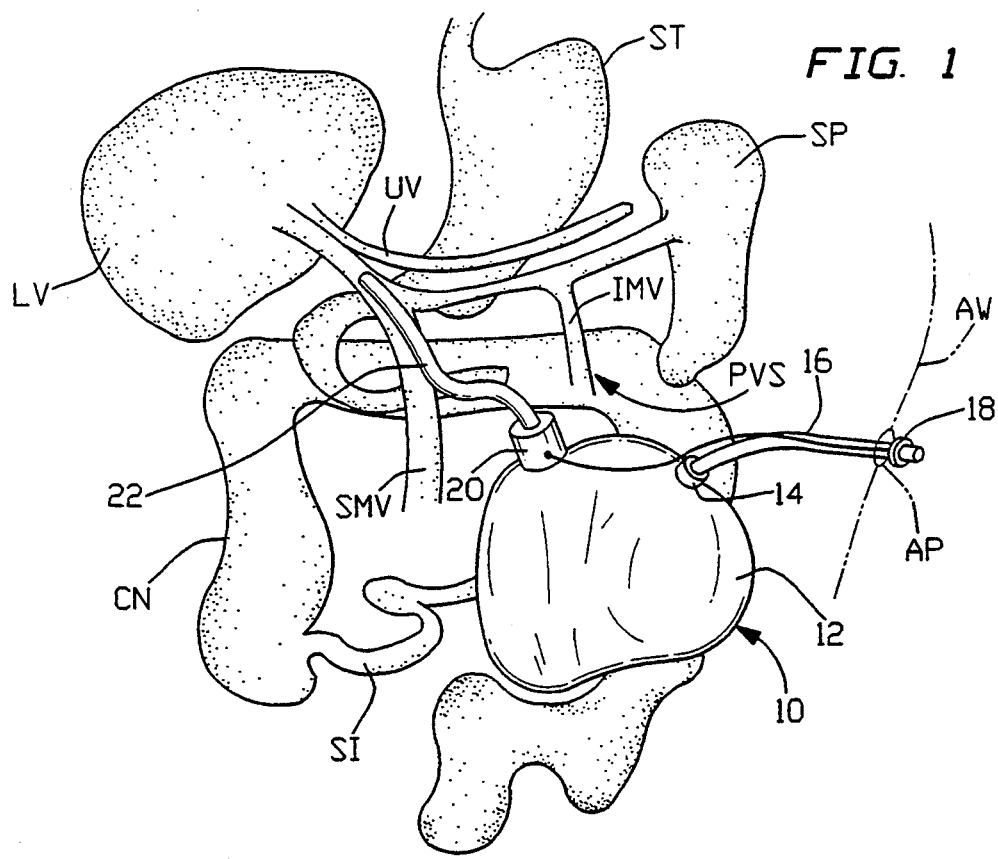
FIG. 1 is a diagram of abdominal organs of a patient, schematically showing an implanted nutrition reservoir assembly.

As illustrated in FIG. 1, an individual's abdominal organs include the stomach ST, the liver LV, the spleen SP, the colon CN, the small intestine SI and the portal vein system PVS. The portal vein system PVS includes blood vessels which extend from the intestines CN and SI to the liver for delivering thereto nutrient carrying blood for processing by the liver LV. The portal vein system PVS includes the superior mesenteric vein SMV, the inferior mesenteric vein IMV, the spleen vein SV and the umbilical vein UV.

As further illustrated in FIG. 1, an assembly 10 for supplying total parenteral nutrition has been surgically implanted into the abdomen. The nutrition assembly 10 basically comprises a reservoir or container 12 which is implanted to rest on the pelvic rim PR.

Container 12 has an inlet port 14 which is surgically connected via a tube or conduit 16 to a port component 18 disposed in the abdominal wall AW of the patient. A pump 20 is mounted to container 12 at an outlet thereof. A tube or outlet conduit 22 extends from pump 20 to the superior mesenteric vein SMV where the distal end of the outlet conduit has been surgically inserted.

It is to be noted that outlet conduit 16 may be connected at its distal end to virtually any vein of the portal vein system, including, but not limited, to the superior mesenteric vein, the inferior mesenteric vein and the spleen vein.

Container 12 holds a supply of a liquid nutritive solution for feeding by pump 20 directly into the portal vein system and from thence to the liver. The feeding of the liquid nourishment to the portal vein system is considered more efficient than the conventional feeding to a vein in the chest inasmuch as nutritive substances need not be carried around the body prior to extraction by the liver for processing.

Container 12 is surgically inserted into the abdominal cavity AC of the patient so that the container rests on pelvic rim PV. The disposition of container 12 may be effectuated through open surgery or laparoscopically. In the latter technique, container 12 must be of sufficient flexibility to permit collapse and folding into a configuration small enough to fit down a laparoscopic cannula or trocar sleeve. Upon insertion of the collapsed bag into the abdomen, the bag is opened and positioned, via the use of laparoscopic gaspers.

Container 12 is accordingly made of a flexible biocompatible material such as silicone or a nonbioabsorbable polymeric composition.

An outlet of container 12 (at pump 20) is surgically connected to a selected vein in the portal vein system PVS so that container 12 communicates with liver LV via the container outlet and the selected vein. The connection of outlet conduit 16 to the portal vein system PVS may be implemented after the disposition of container 12 in the abdomen. Alternatively, it is possible to connect conduit 16 first to the portal vein system and subsequently to container 12. In the latter event, it is particularly necessary to test the integrity of the connection of the conduit 16 to container 16, or to pump 20, to ensure that liquid nutrient does not leak into the abdomen. In fact, the entire parental nutrition system should be tested after installation to ensure the integrity of all lines and connections. During such testing, pump 20 is operated to move liquid nutrient from container 12 to the selected vein in the portal vein system PVS.

During the surgical implantation procedure, port component 18 is positioned in an aperture AP formed in the abdominal wall AW and is connected to inlet port 14 via tube or conduit 16. Upon the disposition of container 12 in the abdomen and the connection of the container to port component 18 via inlet conduit 16, port component 18 may be connected to an external source of nutrient (not shown). The nutrient is fed from the external source to container 12 via port component 18, inlet conduit 16 and inlet port 14. This feeding, which may take place periodically after the completion of the operation in order to refill container or reservoir 14, should be tested prior to the completion of the implantation operation to ensure effective system operation.

Figure 2:
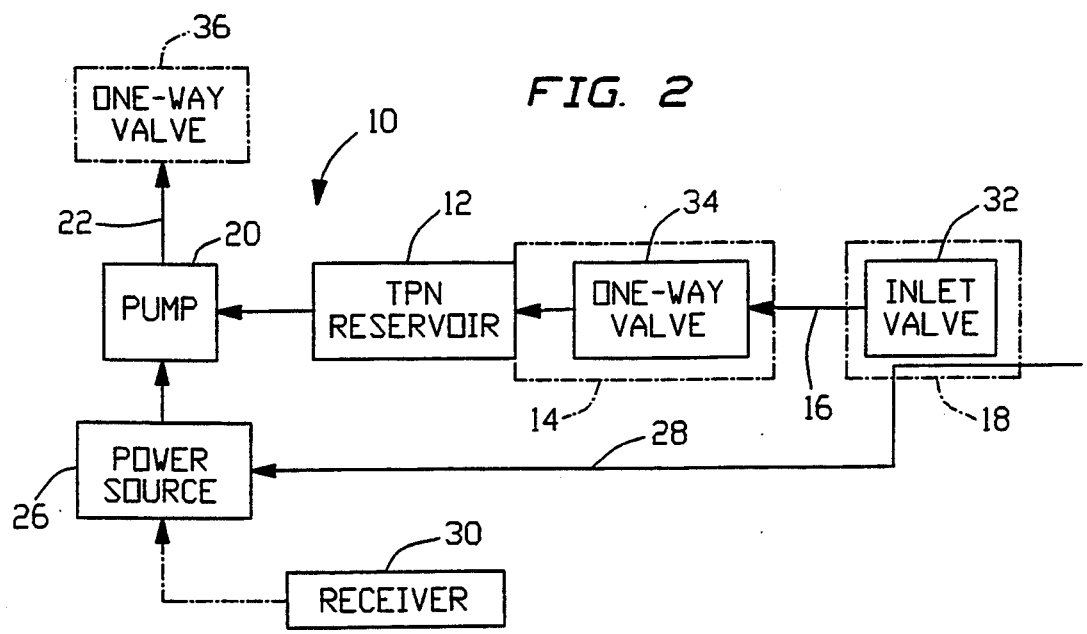
FIG. 2 is a block diagram of operative components of the implanted nutrition reservoir assembly of FIG. 1.

As illustrated in FIG. 2, container 12 is provided with a power source 26 operatively connected to pump 20 for energizing the pump. Power source 26 may be periodically energized or charged from a power supply (not shown) outside the patient's body. The charging of power source 26 may be effectuated by connecting power source 26 to the external power supply via a lead 28 extending through the abdominal wall AW of the patient. More particularly, lead 28 extends to port component 18 where an electrical contact may be formed. Alternatively, pump 20 is connected to a wireless energy receiver 30 which is attached to container 12 and which functions to extract power from an incoming wireless beam of electromagnetic or magnetic radiation.

Upon completion of implantation, the user or patient may periodically connect port component 18 to an external supply of a liquid nutrient for purposes of replenishing the supply in reservoir or container 12. Upon a disconnection of the external supply from port component 18, the port component is closed (e.g., with a cap, not illustrated). Upon the filling of container 12, an amount of the nutritive composition is continuously or periodically pumped by pump 20 from container 12 to the patient's liver LV via the portal vein system PVS.

As further illustrated in FIG. 2, the total parenteral nutrition assembly 10 further includes an inlet valve 32 at port component 18 and another one-way valve 34 at inlet port 14. A one-way valve 36 may additionally be provided in the output line extending to the portal vein system PVS.

Figure 3:
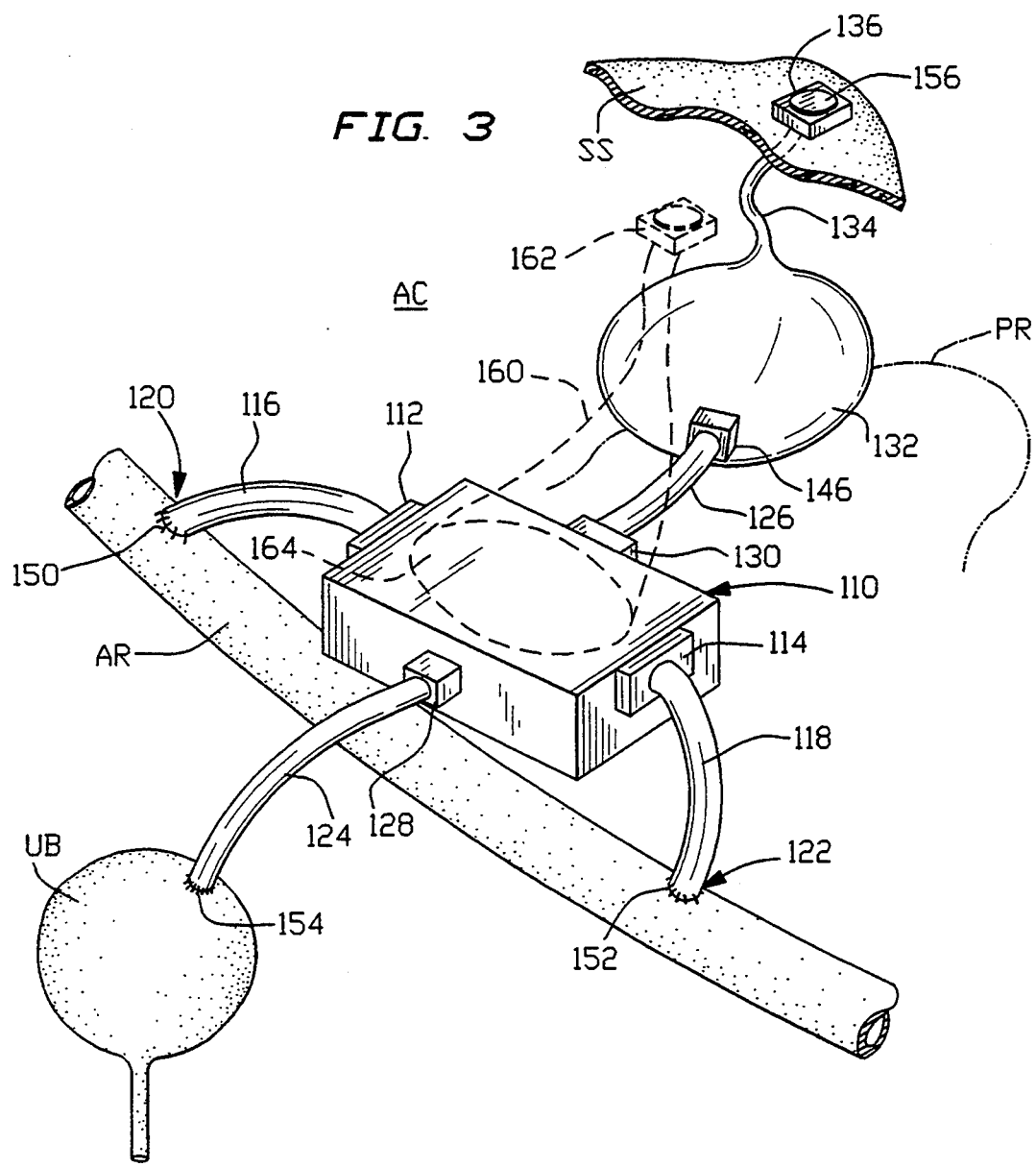
FIG. 3 is a schematic perspective view of a filtering device in accordance with the present invention, showing the device installed in a patient's abdominal cavity.

As depicted in FIG. 3, a filtering device for removing one or more toxic chemical substances from a patient's vascular system includes a housing 110 with a first inlet port 112 and a first outlet port 114 connected via respective grafts or shunts 116 and 118 to an iliac artery AR of the patient, at a relatively upstream point 120 and a relatively downstream point 122, respectively. Shunts 116 and 118, together with ports 112 and 114 and housing 110, define a flow path for blood from artery AR through the filtering device.

A second fluid flow path is defined in part by housing 110 and tubes 124 and 126. Tube 124 connects another outlet port 128 of housing 110 to the urinary bladder UB of the patient, while tube 126 couples another inlet port 130 of housing 110 to a working fluid reservoir 132. Reservoir 132 has a feed tube 134 extending to a feed port 136 disposed in an abdominal skin surface SS of the patient.

Figure 4:
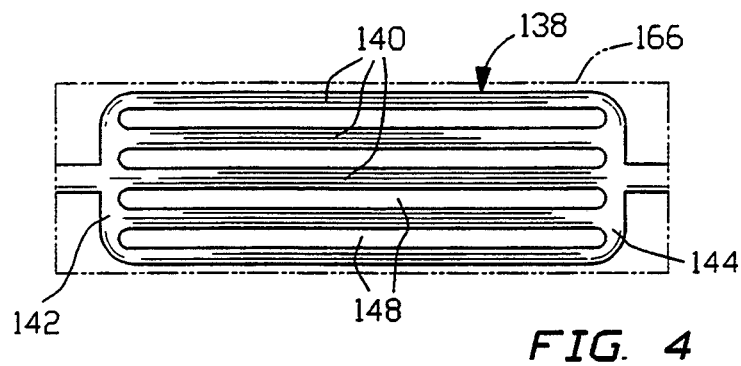
FIG. 4 is a schematic side elevational view of a semipermeable membrane manifold utilizable in the filtering device of FIG. 3.

Housing 110 is provided with a semipermeable membrane 138 (FIG. 4) which separates the blood flow path from the flow path extending between reservoir 132 and urinary bladder UB. As illustrated in FIG. 4, membrane 138 may be provided on a plurality of path branches 140 extending between an inlet manifold 142 at inlet port 112 and an outlet manifold 144 at outlet port 114. Each branch 140 may itself be formed as a plurality of parallel tubes (not shown). A working fluid (not designated) is moved by a pump 146 from reservoir 132 through spaces 148 between branches 140 and then out of housing 110 and through tube 124 to urinary bladder UB. During the pumping of fluid along the flow path extending from reservoir 132 to bladder UB, blood flows along the flow path established by ports 112 and 114 and path branches 140. Concurrently, a target molecular substance in the blood passes through membrane 138 to the working fluid in the second flow path. Thus, the target molecular substance is collected and delivered to urinary bladder UB for periodic discharge from the patient pursuant to natural evacuation processes. Membrane 138 is selected so as to be permeable to the target molecular substance. Compositions of selectively permeable membranes are well-known in the filtration arts. Such membranes are used, for example, in conventional hemodialysis.

The filtering device may comprise housing 110, reservoir 132, and pump 146 as components pre-assembled to one another and inserted into the patient during a surgical procedure. The device is implanted into the patient so that the device is essentially hidden inside the patient's abdominal cavity AC. The surgical operation includes the step of connecting inlet port 112 and outlet port 114 to artery AR at spaced points 120 and 122 along the artery. This connection may be implemented by placing sutures 150 and 152 at the free ends of shunts 116 and 118, in the artery AR. Outlet 128 of housing 110 may similarly be connected to urinary bladder UB via tube 124 and sutures 154.

Further steps of the surgical procedure for employing the filtering device include disposing feed or inlet port 136 at skin surface SS of the patient. Port 136 includes a plug or valve 156 for closing the port and enabling a periodic refilling of reservoir 132 with working fluid.

Upon installation of the filtering device in the patient, pump 146 is operated to transfer working fluid along the second fluid flow path from reservoir 132 to urinary bladder UB while blood flows along the first fluid flow path. Thus, the target toxic substance is transferred from the patient's blood through membrane 138 to the working fluid in the second fluid flow path.

Reservoir 132 is advantageously placed on a pelvic rim PR of the patient, thereby supporting the reservoir and facilitating the filling of a greater volume of reservoir 132 with the working fluid.

As illustrated in dashed lines in FIG. 3, the filtering device may be provided with an access channel 160 extending from an auxiliary port 162 at the patient's skin surface SS to a trap door 164 provided on housing 110. Semipermeable membrane 138 may be attached to a frame or casing 166 (FIG. 4) which is removably inserted into housing 110. Upon a poretermined amount of use of the device, frame or casing 166 may be removed from housing 110 through access channel 160 and port 162. A new semipermeable membrane is subsequently inserted through port 162 and channel 160.

It is to be noted that small pumps are available as off-the-shelf components. Pump 146 could be coated, if necessary, with a conventional biocompatible material such as silicone or some other polymeric material.

Shunt 116 guides blood from the patient's vascular system, i.e., iliac artery AR, to housing 110, where the blood is filtered for removing the target substance from the blood. The cleaned blood is returned to the person's vascular system (artery AR) via shunt 118 upon filtering of the toxic substance from the blood. The toxic substance is delivered to the patient's urinary bladder UB for subsequent elimination.

As discussed hereinabove with respect to pump 20 of FIGS. 1 and 2, pump 146 of FIG. 3 may include a power source with a lead or a wireless power receiver operatively connected to the power source for enabling a periodic recharging of the power source.

Although the invention has been described in terms of particular embodiments and applications, one of ordinary skill in the art, in light of this teaching, can generate additional embodiments and modifications without departing from the spirit of or exceeding the scope of the claimed invention. For example, the filtering device of FIGS. 3 and 4 may be connected to a vein, such as the iliac vein, rather than an artery.

Accordingly, it is to be understood that the drawings and descriptions herein are proffered by way of example to facilitate comprehension of the invention and should not be construed to limit the scope thereof.

What is claimed is:

1. A method for removing a toxic substance from a patient, comprising the steps of:
   (i) providing a filtering device including a first fluid flow path having a first inlet port and a first outlet port and further including a second fluid flow path having a second inlet port and a second outlet port, said filtering device also including a semipermeable membrane separating said first fluid flow path and said second fluid flow path from one another, said membrane being selectively permeable to the toxic substance, said filtering device additionally including a reservoir and a pump, said reservoir being located along said second fluid flow path between said membrane and said second inlet port;
   (ii) inserting said filtering device into the patient so that said filtering device is totally surrounded by the patient;
   (iii) connecting said first inlet port and said first outlet port to a vascular system of the patient at spaced points along said vascular system;
   (iv) attaching said second outlet to the urinary bladder of the patient;
   (v) locating said second inlet port at the skin surface of the patient to enable a periodic refilling of said reservoir with a working fluid;
   (vi) upon completion of steps (i) through (v), operating said pump to transfer working fluid along said second fluid flow path from said reservoir to the urinary bladder of the patient while blood flow along said first fluid flow path, thereby enabling transfer of said toxic substance from the patient's blood through said membrane to said working fluid in said second fluid flow path;
   (vii) upon completion of steps (i) through (vi), removing said semipermeable membrane from said filtering device through an additional port provided at the patient's skin surface; and
   (viii) upon removal of said semipermeable membrane, inserting a new semipermeable membrane into said filtering device through said additional port.

2. The method defined in claim 1, further comprising the step of filling said reservoir with working fluid via said second inlet port.

3. The method defined in claim 2 wherein said step of filling is performed subsequently to said step of locating.

4. The method defined in claim 1, further comprising the step of disposing said reservoir on a pelvic rim of the patient.

5. A method for removing a toxic substance from a patient, comprising the steps of:
   (a) providing a filtering device including a first fluid flow path having a first inlet port and a first outlet port and further including a second fluid flow path having a second inlet port and a second outlet port, said filtering device also including a semipermeable membrane separating said first fluid flow path and said second fluid flow path from one another, said membrane being selectively permeable to the toxic substance;
   (b) also providing a reservoir and a pump, said reservoir having a third inlet port and a third outlet port;
   (c) inserting said filtering device into the patient so that said filtering device is totally surrounded by the patient;
   (d) connecting said first inlet port to a vascular system of the patient at a first point;
   (e) coupling said first outlet port to said vascular system at a second point downstream of said first point;
   (f) attaching said second outlet to the urinary bladder of the patient;
   (g) inserting said reservoir into the patient so that said reservoir is totally surrounded by the patient;
   (h) connecting said second inlet port to said third outlet port;
   (i) providing a feed port at the skin surface of the patient;
   (j) connecting said third inlet port to said feed port;
   (k) inserting said pump into the patient so that said pump is operatively connected to said reservoir and said filtering device;
   (l) upon completion of steps (a) through (k), operating said pump to transfer working fluid along said second fluid flow path from said reservoir to the urinary bladder of the patient while blood flow along said first fluid flow path, thereby enabling transfer of said toxic substance from the patient's blood through said membrane to said working fluid in said second fluid flow path;
   (m) upon completion of steps (a) through (l), removing said semipermeable membrane from said filtering device through an additional port provided at the patient's skin surface; and
   (n) upon removal of said semipermeable membrane from said filtering device, inserting a new semipermeable membrane into said filtering device through said additional port.

6. The method defined in claim 5, further comprising the step of filling said reservoir with working fluid via said second inlet port.

7. The method defined in claim 6 wherein said step of filling is performed subsequently to said step of locating.

8. The method defined in claim 5, further comprising the step of disposing said reservoir on a pelvic rim of the patient.

9. A medical treatment assembly for removing a toxic substance from a patient, comprising:
- a filtering device including a housing and provided with means for defining a first fluid flow path and a second fluid flow path, said housing being adapted to be disposed completely within the patient, said filtering device being adapted to be connected to a vascular system of the patient so that blood from said vascular system flows along said first fluid flow path;
- a semipermeable membrane removably disposed in said housing, said membrane separating said first fluid flow path and said second fluid flow path from one another, said membrane being selectively permeable to the toxic substance, said housing being provided with door means for enabling replacement of said semipermeable membrane upon a disposition of said housing within the patient;
- a reservoir disposed along second fluid flow path upstream of said membrane, said reservoir being adapted to be disposed completely within the patient, said reservoir being operatively connected to said housing via said means for defining; and
- a pump operatively connected to said housing to pump a working fluid along said second fluid flow path from said reservoir and past said semipermeable membrane, thereby enabling transfer of said toxic substance from the patient's blood through said membrane to said working fluid in said second fluid flow path, said housing being operatively connectable to the patient's urinary bladder via said means for defining so that working fluid with the filtered toxic substance flows from said housing to the patient's urinary bladder.

10. The assembly defined in claim 9, further comprising means operatively connected to said housing and connectable to a skin surface of the patient for defining a channel extending from said door means to the patient's skin surface for facilitating membrane substitution.

11. A method for removing a toxic substance from blood, comprising the steps of:
- guiding blood from a person's vascular system to a filtering device implanted in the person;
- filtering the toxic substance from the blood flowing through said filtering device to thereby clean the blood of said toxic substance, said step of filtering including the step of selectively passing the toxic substance through a semipermeable membrane in said filtering device;
- upon filtering of the toxic substance from the blood flowing through said filtering device, returning the cleaned blood to the person's vascular system;
- feeding the filtered toxic substance to the person's urinary bladder;
- removing said semipermeable membrane from said filtering device a port provided at a skin surface of the patient; and
- upon removal of said semipermeable membrane from said filtering device, inserting a new semipermeable membrane into said filtering device through said port.

12. The method defined in claim 11 wherein said working fluid is directed from a reservoir inside the person's abdominal cavity.

13. The method defined in claim 12 wherein said step of directing includes the step of pumping said working fluid from said reservoir and through said filtering device.

14. The method defined in claim 11 wherein said steps of guiding, filtering, returning and feeding all take place within the person's abdominal cavity.

* * * * *

UNITED STATES PATENT AND TRADEMARK OFFICE
CERTIFICATE OF CORRECTION

PATENT NO. : 5,397,354   Page 1 of 2
DATED : March 14, 1995
INVENTOR(S) : Peter J. Wilk and Steven J. Gruber It is certified that error appears in the above-indentified patent and that said Letters Patent is hereby corrected as shown below:

Column 3, line 24, insert --the-- after "along".

Column 4, line 38, change "16" to --22--; line 68, change "16" to --22--.

Column 5, line 3, change "16" to --22--; line 6, change "16" (first occurrence) to --22--; line 6, change "16" (second occurrence) to --12--; line 8, change "parental" to --parenteral--; line 25, change "14" to --12--.

Column 6, line 13, change "on" to --with--.

Column 7, line 2, change "poretermined" to --predetermined--; line 58, claim 1, insert --port-- after "outlet"; line 66, claim 1, change "flow" to --flows--.

Column 8, line 56, change "flow" to --flows--.

UNITED STATES PATENT AND TRADEMARK OFFICE
CERTIFICATE OF CORRECTION

PATENT NO. : 5,397,354
DATED : March 14, 1995
INVENTOR(S) : Peter J. Wilk and Steven J. Gruber It is certified that error appears in the above-indentified patent and that said Letters Patent is hereby corrected as shown below:

Column 9, line 28, claim 9, insert --said-- after "along".

Signed and Sealed this

Tenth Day of October, 1995

Attest:

BRUCE LEHMAN

*Attesting Officer*    *Commissioner of Patents and Trademarks*